United States Patent [19]

Engel

[11] 4,288,221

[45] Sep. 8, 1981

[54] DURABLE, POLISHABLE DIRECT FILLING MATERIAL

[75] Inventor: Michael R. Engel, White Bear Lake, Minn.

[73] Assignee: Minnesota Mining and Manufacturing Company, St. Paul, Minn.

[21] Appl. No.: 115,741

[22] Filed: Jan. 28, 1980

[51] Int. Cl.$^3$ .................... A61C 13/08; C08L 77/00
[52] U.S. Cl. .................................... 433/202; 433/199; 433/228; 525/176; 525/179; 525/182; 525/420; 525/421; 525/426; 525/445
[58] Field of Search ............... 525/420, 421, 426, 437, 525/445, 176, 179, 182; 433/199, 202, 228; 260/40 R, 42, 16, 42.53, 42.54

[56] References Cited

U.S. PATENT DOCUMENTS

| | | | |
|---|---|---|---|
| 3,066,112 | 11/1962 | Bauer | 528/271 |
| 3,338,985 | 8/1967 | Magat et al. | 525/445 |
| 3,503,128 | 3/1970 | Boyd et al. | 528/271 |
| 3,923,740 | 12/1975 | Schmitt et al. | 433/202 |
| 4,020,557 | 5/1977 | Rockett et al. | 433/202 |

FOREIGN PATENT DOCUMENTS 50674  7/1974  Australia ........................... 433/202

OTHER PUBLICATIONS

"Dental Applications," Encyclopedia of Polymer Sci. & Technology, 4, 727–728, 734–736, (Wiley), 1966.
"Handbook of Dental Restortives," Lee et al., 1973, pp. 2,20–2,21.

*Primary Examiner*—J. Ziegler
*Attorney, Agent, or Firm*—Cruzan Alexander; Donald M. Sell; Dean P. Edmundson

[57] ABSTRACT

A curable composite direct filling composition, comprising a polymerizable resin containing at least one acrylic monomer and a finely divided organic filler having an Izod milled notch strength of at least about 1 joule/cm and a flexural strength of at least about 34 MPa.

15 Claims, No Drawings

DURABLE, POLISHABLE DIRECT FILLING MATERIAL

BACKGROUND OF THE INVENTION

This invention relates to curable composite direct filling materials for dental restoration. More particularly, it relates to compositions containing an organic filler.

Direct filling materials are compositions useful for repairing damaged teeth in situ. Direct filling materials containing curable acrylic binder resins such as methyl methacrylate, the reaction product of bisphenol A with glycidal methacrylate, and other resins containing acrylic functionality together with suitable catalysts such as peroxides, hydroperoxides, and photoinitiators (e.g. benzoin ethers) have been widely used for repairing teeth due to their realistic appearance and ease of preparation and use, see "Dental Applications," Encyclopedia of Polymer Science and Technology, 4, 727 (Wiley, 1966). In addition, such resins have also been used to manufacture artificial teeth and denture bases, id at 728, 733. Unfilled (i.e., pure) curable acrylic binder resins generally suffer from polymerization shrinkage and poor durability. These drawbacks have been reduced in direct filling applications, in part, through the addition of inert fillers (see U.S. Pat. No. 3,066,112). The combination of binder plus filler is commonly referred to as a composite direct filling material. Currently used fillers for curable acrylic binder resins generally are inert inorganic materials in the form of finely divided irregular particles, fibers or beads, present in from about 35 to about 80 percent by weight of the total composite direct filling material. Many publications have stressed that suitable filler materials should have low coefficient of thermal expansion, high compressive strength, and high Rockwell Hardness in order to prevent loosening of the cured direct filling material, increase wear resistance, and reduce polymerization shrinkage, see U.S. Pat. Nos. 3,066,112, and 3,503,128, "Dental Applications" id at 734–736, and Lee, Orlowski, and Kobashigawa, *Handbook of Dental Restoratives* (1973) pg. 2.20–2.21.

Commonly used inorganic fillers include fused silica, quartz, glass, various mineral silicates (e.g. $\beta$-eucryptite, lepidolite, petalite, spodumene, beryl, topaz and zircon), silicon carbide, and alumina. In general, composite direct filling materials which are fully loaded with inorganic fillers (i.e. combined with the highest workable volume loading) are the most wear-resistant currently available composite direct filling materials. However, composite direct filling materials containing finely divided inorganic fillers and acrylic binder resins do not polish as easily as unfilled acrylic binder resin.

U.S. Pat. No. 3,923,740 describes a composite direct filling material containing finely divided cured polymethyl methacrylate as a filler, alone or in conjunction with an inorganic filler. Composite direct filling materials which are wholly or partly filled with finely divided polymethyl methacrylate have better polishability (i.e. better surface finish after polishing with ordinary dental tools) than composite direct filling materials which are fully loaded with inorganic fillers, but generally have poorer durability (i.e. poorer wear resistance in vivo) than such fully inorganically filled composite direct filling materials.

It is an object of the present invention to provide a composite direct filling material with an abrasion resistant, resilient surface that has greater durability than composite direct filling materials (that are fully loaded with inorganic materials) while providing good polishability. It is an additional object of the present invention to provide a composite direct filling material with low polymerization shrinkage and low solubility in mouth fluids. It is an additional object of the present invention to provide a dental restorative material useful for the manufacture of replacement teeth or denture bases. Further objects and advantages of the present invention will become apparent from the following description of the invention.

SUMMARY OF THE INVENTION

The present invention provides, in one aspect, a composite dental restorative composition, comprising a blend of:
(A) free radically polymerizable resin comprising at least one acrylic monomer; and
(B) finely divided organic filler particles, said filler having an Izod milled notch strength of at least about 1 joule/cm and a flexural strength of at least about 34 MPa; which composition in reactive association with a free radical generating catalyst will cure into a direct filling material.

DETAILED DESCRIPTION OF THE INVENTION

In the practice of the present invention, the polymerizable resin is an acrylic resin, that is, a resin containing at least one acrylic monomer, alone or with other comonomers which will polymerize with the acrylic monomer to form a polymer containing repeating acrylic linkages. Suitable polymerizable resins include methyl methacrylate and the resin known as "BIS-GMA" and corresponding to a reaction product formed by combining Bisphenol A with glycidyl methacrylate or by combining the diglycidyl ether of Bisphenol A with methacrylic acid (said reaction product being optionally diluted with a reactive diluent such as triethylene glycol bis methacrylate). BIS-GMA is the preferred polymerizable resin. The resin, when cured into the shape desired for dental restorative purposes, acts as a binder which envelops the filler, thereby forming a material whose working surface is polishable and has good resistance to abrasive conditions commonly present in the human mouth.

The finely divided organic filler is a durable plastic material having an Izod milled notch strength (as measured according to ASTM D-256-78 using a 0.25 mm notch radius) of at least about 1 joule/cm, preferably at least about 2.67 joules/cm, and most preferably at least about 8 joules/cm, and a flexural strength (as measured according to ASTM D-790-71 (reapproved 1978), Method I) of at least about 34 MPa and preferably at least about 69 MPa. Materials which do not fracture during an Izod milled notch strength test or which do not fail during a flexural strength test (using Method II) will be deemed to exceed the above Izod milled notch strength requirement of about 8 joules/cm or the above flexural strength requirement of about 69 Mpa, respectively. Suitable filler materials include polyesters such as polyethylene terephthalate and polybutylene terephthalate and polyamides such as poly (6-amino hexanoic acid) and poly (hexanedioic acid/hexamethylene diamine). Nylons having a high Izod milled notch strength such as the "Zytel 800" series of nylons commercially available from E. I. duPont de Nemours & Co. are preferred organic fillers for use in the present invention.

The organic filler should be included in compositions of the present invention in amounts between about 35 to 80 percent by weight of the total composition, preferably about 50 to 70 percent by weight. The fillers used in the present invention have good toughness, durability, and resiliency. When mixed with the polymerizable binder resin, a composite direct filling material is formed which, when cured, tends to absorb impact and wear to a surface which is smooth when viewed under an optical microscope. In contrast, composite direct filling materials filled with inorganic fillers do not wear evenly. Inorganic filler particles lack resilience and tend to pop loose from the surface of a cured composite material when subjected to abrasion, resulting in a surface which is uneven and pitted when viewed under an optical microscope. Filler particles made from finely divided polymethyl methacrylate lack toughness and durability and cured composite materials containing such fillers tend to wear quickly.

The organic fillers used in the present invention differ in several respects from the characteristics which have been described as important by other workers in the field of dental restorative resins. It is not important that the organic fillers used in the present invention have a Rockwell Hardness higher than that of the polymerized binder resin. In fact, the fillers used in the present invention may have a Rockwell Hardness lower than that of the polymerized binder resin without adversely affecting durability. Also, it is not important for purposes of the present invention that the filler have a coefficient of thermal expansion near that of tooth enamel. The fillers used in the present invention generally have coefficients of thermal expansion nearer that of the polymerized binder resin than that of tooth enamel, yet exhibit good durability. Finally, while low water absorption is desirable, the fillers used in the present invention may have water absorption higher than that of the polymerized binder resin, yet still form useful composite direct filling materials. In comparison with the inorganic fillers of the prior art, the organic fillers used in the present invention have generally lower Rockwell Hardness, generally higher coefficient of thermal expansion, and generally higher water absorption. In comparison with prior art fillers made of finely divided methylmethacrylate resin, the organic fillers used in the present invention have generally lower Rockwell Hardness, generally higher coefficient of thermal expansion, and generally higher water absorption.

The filler particles used in the present invention are finely divided or granulated and are in the form of regularly or irregularly shaped particles, spheres, rods, or fibres ranging in mean diameter from about 2 to 100 micrometers, and preferably from about 5 to 50 micrometers. A composite direct filling material filled with a mixture of small and large generally spherical filler particles with a size ratio of between about 1 to 7 and 1 to 10 is somewhat easier to pack into a dental restorative cavity than is a composite direct filling material filled with generally spherical particles of uniform size, and is preferred. Suitably sized filler particles of nylon or other fillers of the present invention may be made using conventional grinding and classifying methods, and optionally may include exposure of the ground particles to heat to smooth their rough edges. Suitably sized generally spherical particles of nylon may be made by extruding a mixture of granular nylon and granular polystyrene through a die heated to approximately 280° C. and cooling the extrudate by quenching in air. Because nylon and polystyrene are incompatible, the nylon will form microspheres in the molten polystyrene. The cooled nylon microspheres may be isolated by dissolving away the polystyrene with a solvent such as chloroform.

If desired, a keying agent (primer) may be coated upon the filler particles or added to the polymerizable resin in compositions of the present invention in order to improve adhesion of the filler particles to the polymerized binder resin. No keying agent is ordinarily required for nylon or polyester fillers.

When mixed with a catalyst or initiator capable of generating free radicals, the compositions of the present invention will cure or harden into durable composite direct filling dental restorative materials. Suitable catalysts include peroxides, hydroperoxides, dinitriles, and redox catalyst systems. Specific catalysts include benzoyl peroxide, methyl ethyl ketone peroxide, tertiary butyl hydroperoxide, and tertiary butyl perbenzoate. Such catalysts may be used with various accelerators, preferably aromatic amines, forming a two-part system.

Compositions of the invention are also polymerized rapidly by exposure to light of wavelengths shorter than 500 nm, e.g., ultraviolet light, when they contain known free radical forming aromatic ketonic catalysts, such as benzoins, acetophenones, aromatic diketones, etc. with or without appropriate aliphatic amine accelerators such as dimethylaminoethyl methacrylate, triethanolamine. Such compositions form useful one-part systems which are generally stable to ambient light conditions.

Useful representative accelerators include N,N-bis(-hydroxyethyl)-p-toluidine, N,N-dimethyl-p-toluidine, N,N-bis(hydroxy-lower alkyl)-3,5-xylidines, p-toluenesulfinic acid, 1,3,5-trimethyl barbituric acid, 1-benzyl-5-phenyl-barbituric acid and 5-butyl barbituric acid. For two part systems which polymerize readily when mixed the composition is used in two portions one of which includes the catalyst and the other the accelerator. The polymerizing composition should contain about 0.5 to about 2 percent by weight of catalyst and about 1 to about 3 percent by weight of accelerator. The concentration in the respective parts are so adjusted that predetermined amounts of each are mixed immediately before polymerization is to be initiated, using, for example, a spatula and palate. The mixture is applied to a prepared tooth surface and polymerization then occurs in about 0.5 to 10 minutes. For UV-polymerizable systems the composition is used in one part containing from about 0.5 to about 2 percent by weight of catalyst and up to about 3 percent by weight of accelerator. The composition is applied to a prepared tooth surface. When exposed to light of less than 500 nm wavelength such a composition will polymerize in from a few seconds to about 1 minute.

The compositions of the present invention may also be used in one part systems containing catalyst but no accelerator. These systems are applied directly to a prepared tooth surface and thermally cured. After the dental restoration has cured, the restorative material can be polished. The surface can be brought to a state that is smoother to the touch than that obtainable with an inorganically filled composite direct filling material. The surface smoothness of the composite direct filling material of the present invention will improve in use, and this contributes in part to the superior wear characteristics of the organically filled composite direct filling materials of the present invention compared to inorganically filled composite direct filling materials.

The composite direct filling materials of the present invention are more opaque than tooth enamel and some inorganically filled composite direct filling materials. Inorganically filled composite direct filling materials may, therefore, continue to be preferred in applications where cosmetic appearance is more important than durability (e.g. the labial surface of an upper front incisor). Also, inorganically filled composite dental restorative materials may continue to be preferred for the manufacture of replacement teeth in applications where cosmetic appearance is more important than durability. However, the composite dental restorative materials of the present invention can be used to make very durable direct fillings, artificial teeth, and denture bases, and their use is not intended to be restricted to any particular region of the mouth.

The following examples are offered to aid understanding of the present invention and are not to be construed as limiting the scope thereof. Unless otherwise indicated, all parts are parts by weight.

EXAMPLE 1

A two part direct filling material was prepared. The first part (referred to hereafter as "Part A") has a total weight of 15 grams and contained the ingredients described below in Table I:

TABLE I

| Ingredient | Parts |
| --- | --- |
| Triethylene glycol bis methacrylate | 8.0 |
| Adduct of the diglycidyl ether of Bisphenol A and methacrylic acid, combined in a 1:2 molar ratio | 12.0 |
| Benzoyl peroxide | 0.30 |
| Butylated hydroxytoluene | 0.004 |
| Bisphenol A (food grade) | 0.024 |
| Nylon microspheres ("Zytel" 801, commercially available from E.I. duPont de Nemours & Co.) | 20.5 |

The nylon microspheres were prepared by extruding granulated nylon and granulated polystyrene as described above, resulting in microspheres whose mean diameters ranged from about 5 to about 50 micrometers as measured by examination under optical microscope. The ingredients were mixed by spatulation and set aside. A second part (referred to hereafter as "Part B") was similarly prepared by combining the ingredients described below in Table II.

TABLE II

| Ingredient | Parts |
| --- | --- |
| Triethylene glycol bis methacrylate | 8.0 |
| Adduct of the diglycidyl ether of Bisphenol A and methacrylic acid, combined in a 1:2 molar ratio. | 12.0 |
| N,N-bis(hydroxyethyl)-p-toluidine | 0.6 |
| 2-(2'-hydroxy-5-methylphenyl) benzotriazole | 0.1 |
| Nylon microspheres ("Zytel" 801) | 20.5 |

Small equal sized spoonfuls of Part A and Part B were combined and mixed by spatulation, resulting in a mixture containing 50 percent filler by weight and approximately 50 percent filler by volume. The mixture was then compressed in a cylindrical mold 1.25 cm in diameter. The mixture cured into a hard mass within about 3 minutes from the time the mixing of Part A and Part B was initiated. The cured cylindrical test sample was demolded.

A reference sample was prepared from the same ingredients used above, but with the substitution of 47.9 parts of finely divided ground quartz for the 20.5 parts of nylon microspheres used in Part A and Part B (resulting in a mixture containing 70 percent filler by weight and approximately 50 percent filler by volume). The reference sample was molded and cured as described above.

The test and reference samples were then evaluated as follows. The test and reference samples were machined flat. Bovine enamel was machined to a $\frac{1}{4}''\times\frac{1}{4}''$ surface and mounted in a fixed mandrel. The test sample was mounted in a motor-driven mandrel and rotated against the machined bovine enamel surface at a speed of 500 to 1000 rpm and under a force of approximately 1 kg. The test sample disk surface was immersed in a 25 percent solution of ethylene glycol in water. After one hour, the test sample is removed, washed, and dried overnight in an incubator at 37° C. The reference sample was then rotationally abraded, washed, and dried in the same fashion. Both the test and reference samples were weighed. The test and reference samples were then alternately rotationally abraded in the above described test apparatus for a series of 30 minute periods until both the test and reference samples had accumulated an eight hour abrasion time after the initial weighing. The test sample and reference sample weights were monitored during the abrading sequence described above by washing in distilled water, absolute alcohol, and ether at the conclusion of each 30 minute abrading period, drying in a dessicator for 30 minutes, and then weighing. At the conclusion of the abrading sequence the test and reference samples were washed, dried overnight at 37° C. in an incubator, and weighed a final time.

A comparison of the change in weight for the test and reference samples indicated the relative difference in wear rates. A wear index was calculated using the following formula:

$$\frac{\text{Wear}}{\text{Index}} = \frac{\frac{\text{final } T.S. \text{ weight} - \text{original } T.S. \text{ weight}}{\text{original } T.S. \text{ weight}} \times \text{original } T.S. \text{ thickness}}{\frac{\text{final } R.S. \text{ weight} - \text{original } R.S. \text{ weight}}{\text{original } R.S. \text{ weight}} \times \text{original } R.S. \text{ thickness}} \times 100$$

where
T.S. = test sample
R.S. = reference sample.

If the wear index is 100, then the test sample abrades or wears to the same extent as the reference sample. A wear index below 100 indicates a lower test sample wear rate than the reference sample, and vice-versa. For the nylon filled test sample described above, the wear index was 35.

EXAMPLE 2

Using the method of Example 1, a two part direct filling material was prepared. The composition of the first part (referred to hereafter as "Part C") is set out below in Table III.

TABLE III

| Ingredient | Parts |
| --- | --- |
| Triethylene glycol bis methacrylate | 12.0 |

TABLE III-continued

| Ingredient | Parts |
| --- | --- |
| Adduct of the diglycidyl ether of Bisphenol A and methacrylic acid, combined in a 1:2 molar ratio. | 8.0 |
| Benzoyl peroxide | 0.30 |
| Butylated hydroxytoluene | 0.004 |
| Bisphenol A (food grade) | 0.024 |
| Nylon microspheres ("Zytel" 801, commercially available from E.I. duPont de Nemours & Co.) | 47.9 |

The composition of the second part (referred to hereafter as "Part D") is set out below in Table IV.

TABLE IV

| Ingredient | Parts |
| --- | --- |
| Triethylene glycol bis methacrylate | 12.0 |
| Adduct of the diglycidyl ether of Bisphenol A and methacrylic acid, combined in a 1:2 molar ratio | 8.0 |
| N,N-bis(hydroxyethyl)-p-toluidine | 0.60 |
| 2-(2'-hydroxy-5-methylphenyl) benzotriazole | 0.10 |
| Nylon microspheres ("Zytel" 801) | 47.9 |

A test sample prepared by mixing equal amounts of Part C and Part D (resulting in a mixture containing 70 percent filler by weight) was compared to a reference sample made as described in Example 1. The wear index for the test sample was 14.

EXAMPLE 3

Using the method of Example 2 a test sample was prepared containing 8.8 parts of finely divided nylon particles mechanically ground in Part C and Part D (resulting in a mixture containing 30 percent filler by weight). The wear index for the test sample was 25.

EXAMPLE 4

Using the method of Example 2 a test sample was prepared containing 20.5 parts of poly (6-amino hexanoic acid) microspheres in Part C and Part D (resulting in a mixture containing 50 percent filler by weight). The wear index for the test sample was 50.

EXAMPLE 5

Using the method of Example 2 a test sample was prepared containing 25.1 parts of microcrystalline polyethylene terephthalate (PET) particles in Part C and Part D (resulting in a mixture containing 55 percent filler by weight). The microcrystalline PET particles were prepared by refluxing 10 g 1 mm diameter PET particles for three and one-half hours in a mixture of 3.5 g n-propylamine, 1.75 ml ethylene glycol, and 134.5 ml water. The particles were filtered, water washed three times, dried in air and then pulverized in a mortar and pestle to a 10 micrometer mean particle diameter. The wear index for the test sample was 33.

Various modifications and alterations of this invention will be apparent to those skilled in the art without departing from the scope and spirit of this invention.

What is claimed is:

1. A composite dental restorative composition, comprising a blend of:
   (A) free radically polymerizable resin comprising at least one acrylic monomer; and
   (B) finely divided organic filler particles, said filler having a Izod milled notch strength of at least about 1 joule/cm and a flexural strength of at least about 34 Mpa; which composition in reactive association with a free radical generating catalyst will cure into a direct filling material.

2. A composition according to claim 1, wherein said filler comprises polyamide.

3. A composition according to claim 1, wherein said filler comprises polyethylene terephthalate.

4. A composition according to claim 1, wherein said filler has an Izod milled notch strength of at least 2.67 joules/cm and a flexural strength of at least about 69 MPa.

5. A composition according to claim 1, wherein said filler has an Izod milled notch strength of at least about 8 joules/cm and a flexural strength of at least about 69 MPa.

6. A composition according to claim 5, wherein said filler comprises polyamide.

7. A composition according to claim 1, wherein said filler particles have a mean diameter between about 2 and about 100 micrometers.

8. A composition according to claim 1, wherein said filler particles have a mean diameter between about 5 and about 50 micrometers.

9. A composition according to claim 1, wherein said filler is included in said composition in an amount from about 35 to about 80 percent by weight.

10. A composition according to claim 1, wherein said filler is included in said composition in an amount from about 50 to about 70 percent by weight.

11. An artificial tooth made from a composition according to claim 1.

12. A denture base made from a composition according to claim 1.

13. A two part dental restorative composition, comprising:
   (A) a first blended mixture, comprising
      (1) free radical polymerizable resin comprising at least one acrylic monomer;
      (2) free radical generating catalyst; and
      (3) finely divided organic filler particles, said filler having an Izod milled notch strength of at least about 1 joule/cm and a flexural strength of at least about 34 MPa; and
   (B) a second blended mixture, comprising
      (1) free radically polymerizable resin comprising at least one acrylic monomer;
      (2) aromatic amine accelerator; and
      (3) finely divided organic filler particles, said filler having an Izod milled notch strength of at least about 1 joule/cm anc a flexural strength of at least about 34 MPa; and
   which first and second blended mixtures will, upon admixture with one another, cure into a direct filling material.

14. A composition according to claim 13, wherein said filler comprises polyamide with an Izod milled notch strength of at least about 8 joules/cm, as flexural impact strength of at least about 69 MPa, and is included in said composition in an amount between about 35 to about 80 percent by weight, and said filler particles have a mean diameter between about 2 and about 100 micrometers.

15. A composition according to claim 14, wherein said filler is included in said composition in an amount between about 50 to about 70 percent by weight and said filler particles have a mean diameter between about 5 and about 50 micrometers.

* * * * *